United States Patent [19]
Talaty et al.

[11] 4,149,011
[45] Apr. 10, 1979

[54] NOVEL SUBSTITUTED ALANINES

[75] Inventors: Chandravadan N. Talaty, Athens, Ga.; Jeremy Wright, Baltimore; Nicolas Zenker, Lutherville, both of Md.

[73] Assignee: Merck & Co., Inc., Rahway, N.J.

[21] Appl. No.: 822,485

[22] Filed: Aug. 8, 1977

Related U.S. Application Data

[62] Division of Ser. No. 769,802, Feb. 17, 1977, Pat. No. 4,070,478.

[51] Int. Cl.$^2$ ............................................. C07C 63/52
[52] U.S. Cl. ..................................................... 562/434

[58] Field of Search ......................................... 200/519

[56]  References Cited
U.S. PATENT DOCUMENTS

| 3,023,235 | 2/1962 | Leonard .............................. 260/519 |
| 3,801,633 | 4/1974 | Toyoshima et al. ................. 260/519 |

*Primary Examiner*—James O. Thomas
*Assistant Examiner*—James H. Reamer
*Attorney, Agent, or Firm*—Daniel T. Szura

[57] ABSTRACT

Intermediate compound useful in the preparation of Benzimidazol-5-yl alanine derivatives useful as antihypertensive agents.

1 Claim, No Drawings

NOVEL SUBSTITUTED ALANINES

This is a division of U.S. application Ser. No. 769,802 filed Feb. 17, 1977.

BACKGROUND OF THE INVENTION

The present application is concerned with novel substituted benzimidazolylalanines which are useful as antihypertensive agents.

Unsubstituted 3-(benzimidazol-5-yl)-alanine and 3-(benzimidazol-5-yl)-2-methylalanine are known [see *Journal of Medicinal Chemistry* 4, 741 (1970); Fifth International Congress on Pharmacology, Abstract 964, July 23–28, 1972]. Each of these alanines is known to effect in vivo depletion of norepinephrine in the brain and heart. Neither of these alanines is known to have substantial antihypertensive activity.

3,4-Dihydroxyphenyl-2-methylalanine, also commonly known as methyldopa, is a well known antihypertensive agent. It also is known to effect a substantial depletion of norepinepherine, in vivo, in both the brain and heart.

Novel substituted benzimidazole alanines, specifically 3-(6-hydroxybenzimidazol-5-yl)alanine, 3-(6-hydroxybenzimidazol-2-one-5-yl)alanine and 3-(6-methoxybenzimidazol-2-one-5-yl)alanine have been prepared. These compounds exhibit antihypertensive activity.

SUMMARY OF THE INVENTION 3-(6-Hydroxybenzimidazol-5-yl)alanine, 3-(6-hydroxybenzimidazol-2-one-5-yl)alanine and 3-(6-methoxybenzimidazol-2-one-5-yl)alanine their pharmaceutically acceptable salts and use as antihypertensive agents.

DESCRIPTION OF THE PREFERRED EMBODIMENTS

The present invention is embodied in compounds having the formulae

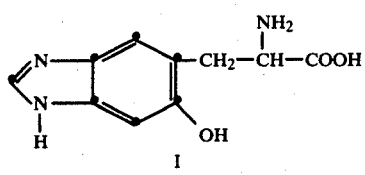

I

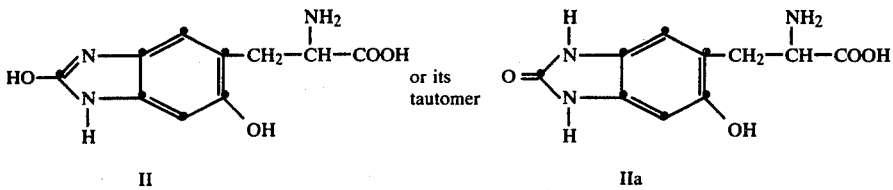

and

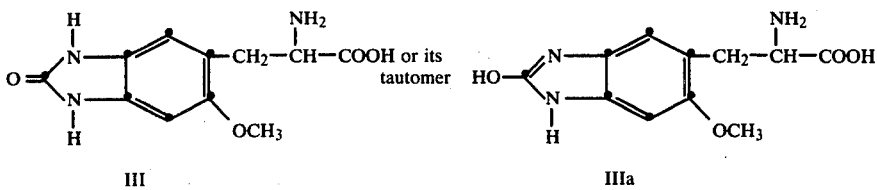

and pharmaceutically acceptable salts thereof. Since each of the Formula I, through IIIa compounds has an asymmetric carbon atom, it is optically active. Thus, these compounds include the individual optical isomers as well as the racemate and other isomer mixtures.

These individual optical isomers are variously designated as l and d, D and L, − and + or by combinations of these symbols. These isomers may also be designated S (sinister) and R (rectus), symbols which indicate the absolute spatial configuration of the isomer molecule.

An appropriate isomer designation may be used in naming a compound. Where no symbol is given, then the compound named includes the individual isomers, the racemate and all isomer mixtures.

Pharmaceutically acceptable salts include metal salts, e.g. sodium, potassium, etc., and the salts of the Formula I–IIIa compound with suitable acids. These acids include inorganic and organic acids. Useful inorganic acids encompass the hydrohalide acids e.g. HCl, HBr, HI, sulfuric acid and phosphoric acid. The organic acids include carboxylic and non-carboxylic acids. The carboxylic acids may contain from 2 to about 24 carbon atoms. Useful carboxylic acids are exemplified by acetic acid, cyclohexylcarboxylic acid, maleic acid, citric acid, hexanoic acid, tetracosanoic acid, oxalic acid, succinic acid, tartaric acid, the fatty acids, e.g., palmitic, oleic, stearic, pamoic and the like, fumaric acid, malic acid, ascorbic acid, pivalic acid and the like. An especially useful non-carboxylic acid is isethionic acid. Pharmaceutically acceptable means that the salts are substantially non-toxic and retain the required pharmaceutical activity.

Preferred salts are the hydrohalides and especially the hydrochlorides and hydrobromides.

Representative salts of the compounds of Formulae I, II and III have been found to effect a reduction in blood pressure when administered to spontaneously hypertensive rats. It is believed that the compounds of the present invention are useful to treat hypertension in animals, including humans. Hypertension manifests itself, and is commonly referred to, as "high blood pressure." Thus, the present compounds are useful in lowering the blood pressure of hypertensive patients.

A representative salt of the Formula I compound has also been found to reduce norepinephrine in the brain and heart of rats using a conventional test procedure.

The dosage required to effect lowering of blood pressure in the hypertensive patient will vary. Daily dosage ranging from 10 to 3500 mg of a compound of Formula I to IIIa is useful. A preferred daily dosage range is 50–1000 mg, with 100–750 mg being more preferred.

The compounds may be administered alone or in combination with suitable pharmaceutical compounding ingredients. Useful dosage forms include those suitable for oral administration, e.g., tablets, capsules, suspensions, emulsions and the like, as well as for parenteral administration, e.g., solution, suspension, emulsion and the like. The dosage forms are prepared using conventional procedures, equipment and compounding ingredients, i.e., diluents, carriers, excipients, encapsulating materials, etc.

In addition to the more conventional administration modes and dosage forms, the present compounds may also be administered in a form which will dispense the compound to the patient continuously over an extended period of time. This method of administration is embodied in a carrier device or means which is imbedded, inserted, attached, ingested or otherwise provided to the patient. An advantage of this form of administration is that it ensures continuous, regulated and convenient administration of the hypertensive agent to the patient.

The following examples illustrates preparation of a representative compounds of the present invention. While the example products obtained are racemates (D,L), they may be separated into the D and L enantiomers by conventional procedures such as resolution using an optically active acid (e.g., tartaric acid) in a suitable solvent system. All temperatures in the example are in degrees centigrade.

EXAMPLE 1

Preparation of D,L-3-(6-hydroxybenzimidazole-5-yl)alanine-.2HBr

A. Diethyl-2-Methoxy-5-Nitrobenzyl acetamido malonate

Molar amounts of 2-chloromethyl-4-nitroanisole and freshly prepared sodiodiethylacetamidomalonate were refluxed in ethanol for 5 hrs. and the turbid solution filtered hot. The filtrate was allowed to cool and refiltered to yield 2-methoxy-5-nitrobenzyl acetamidomalonate A in 70–75% crude yield, m.p. 161°–163°. This crude product was used for the next step as such.

B. Diethyl-2-Methoxy-5-Acetylaminobenzyl-acetamidomalonate

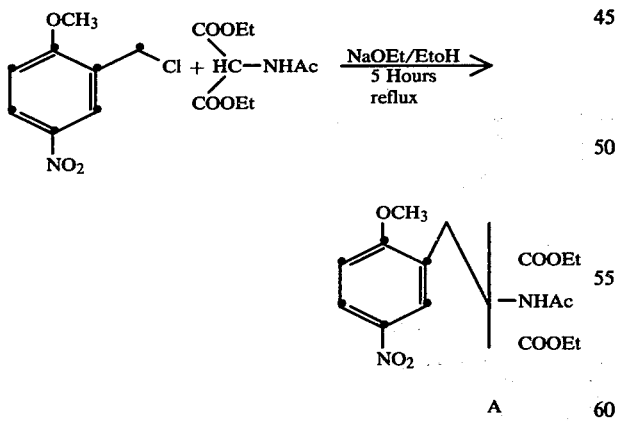

The crude nitro compound A (15 g) from the previous step was dissolved in absolute ethanol (200 ml), Pd-C (10%, 0.8 g) was added and the mixture hydrogenated in a Paar bottle at 40 psi until no more hydrogen was absorbed (2–3 hrs.). The mixture was filtered through Celite (to remove Pd-C) and the filtrate evaporated in vacuo to give the colorless solid amine m.p. 129°–131°. The amine was in all cases directly acetylated by refluxing with acetic acid (5 ml) and acetic anhydride (25 ml) for 1 hour. The mixture was then poured into ice water (100 ml), cooled in the refrigerator for 1 hour, then filtered and the solid washed with water. Drying in vacuo at 60° yielded 13.5 g of the desired acetate B (88%), mp 143°–145°. The crude acetate B was taken up for nitration without further purification. Recrystallization from ethyl acetate yielded an analytical sample of B mp 150°–51°.

C. Diethyl-2-Methoxy-4-Nitro-5-Acetamidobenzylacetamidomalonate:

The crude acetate B from the previous step (15 g) was stirred in a 250 ml 3-necked flask with a 1:1 mixture of acetic acid and acetic anhydride (45 ml). The solution was cooled externally in ice to 0°–5°. Through a dropping funnel, conc. HNO₃ (30 ml) was gradually added while maintaining the temp. below 10° (1 Hr). After stirring for an additional 1 hour at 10°–15°, the reaction mixture was gradually added with rapid stirring to NaHCO₃ (120 g) in 400 ml cold water to bring it to pH 7. The mixture was stirred (30 min.), filtered and washed with water to give 18–20 g of a dark yellow solid, mp 157°–158°. Recrystallization from CHCl₃:Hexane (1:1, 200 ml) yielded 14.7 g (88%) of crystalline yellow compound C, mp 159°–161°.

D. 2-Methoxy-5-Amino-4-Nitrophenylalanine

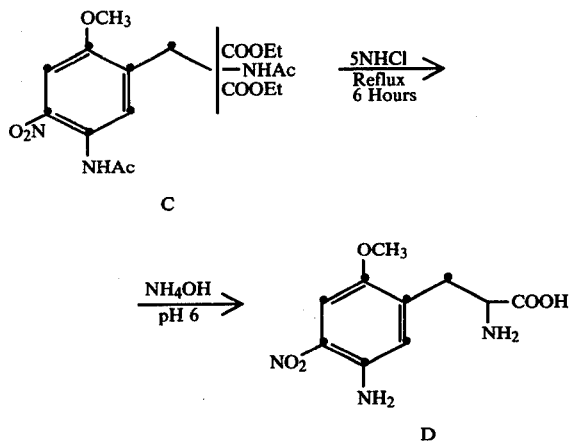

Compound C (10 g) was refluxed with 5N HCl (90 ml) for 6 hours. The solution was then cooled in ice and neutralized with 30% NH₄OH to pH 6, cooled in the refrigerator overnight, filtered and dried in a vacuum oven, or at room temperature, yielding 5.5 g of the crude compound D, mp 232°–234°. However, the compound contained 1 mol of water of crystallization. The yield as hydrate was 88%. The amino acid D was directly used without further purification in most cases. A small amount of the sample was recrystallized from CH₃OH:H₂O (1:1) giving bright red crystals of the hydrate of D m.p. (color changing to pale yellow around 110°) 239°–240° (dec).

E. 5-(6) Methoxy Benzimidazole 6-(5) alanine .HCl

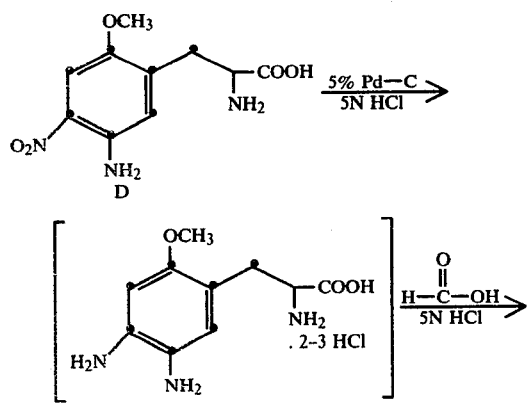

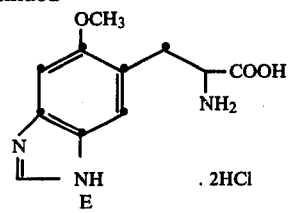

The crude amino acid D (1.0 g) was dissolved in 5N HCl (40 ml) in a Paar bottle, 5% Pd-C (0.1 g) was added and the mixture hydrogenated (1.5–2 hours) at 35–40 psi until no additional H₂ was absorbed. The Paar Bottle was then flushed with N₂ and the contents transferred to a 250 ml flask containing 7 ml formic acid (97%) and 5 ml of 5N HCl. The mixture was refluxed for 3.5 hours with exclusion of air (Hg trap used) and was then stirred (30 minutes) with Norit (a charcoal) and filtered through Celite to give a pale yellow mother liquor. The solvent was then removed in vacuo and the solid obtained was co-evaporated in vacuo twice with 5 ml isopropyl alcohol each time (to remove excess H—COOH and HCl). Finally isopropyl alcohol was added and the mixture refrigerated overnight. The solid was then filtered, washed well with cold isopropyl alcohol, and dried at 110°, 0.1 mm Hg for 5 hours giving 970 mgs of a pale yellow solid, mp 271° (dec.) which was recrystallized from ethanol:water and dried in vacuo to give 620 mgs (51.1%) of compound E, mp 275° (dec.).

F. D,L-3(6-dihydroxybenzimidazol-5-yl) alanine .2HBR

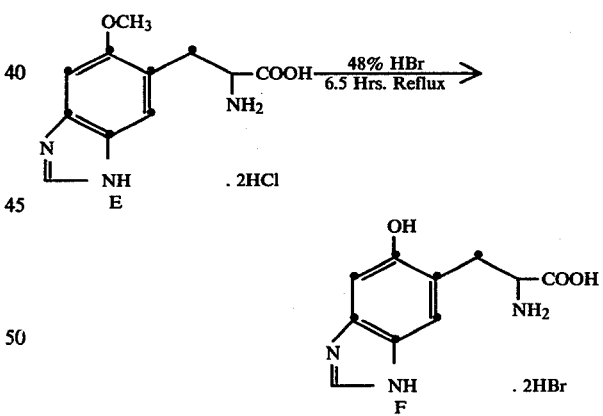

The amino acid E (1.35 g) was refluxed with 48% HBr (25 ml) for 6.5 hours using a Hg trap to exclude air. The solution was cooled in a freezer overnight. The solid that separated on cooling was filtered, washed first with acetone and then with ether. On drying the solid in vacuo at 110°, crude compound F (1.6 g), decomposing at 279°, was obtained. The solid was dissolved in ethanol:H₂O (45:5 ml) and treated with neutral Norit (a charcoal) for 4 hours. After filtering through Celite to remove charcoal, the mother liquor was evaporated in vacuo and the solid recrystallized from ethanol:acetonitrile (1:2) to yield 0.9 g (53.6%) of colorless product F, decomposing at 273°.

EXAMPLE 2

Preparation of
D,L-3-(6-hydroxybenzimidazol-2-one-5-yl)alanine .HBr

A. 3-(6-Methoxybenzimidazol-2-one-5-yl)alanine

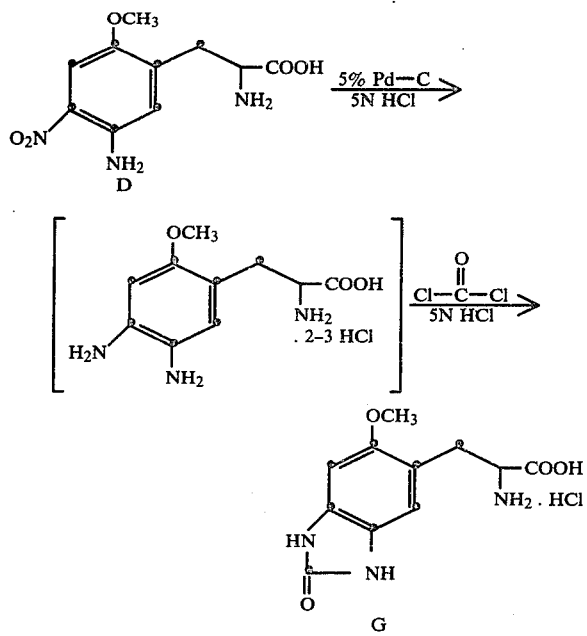

The crude amino acid D (2.5 g) was dissolved in 5N HCl (175 ml), 5% Pd-C (0.25 g) was added and the mixture hydrogenated at 35–40 psi until no more H₂ was absorbed (1.5–2 hrs). The Paar bottle was flushed with N₂ and the contents transferred to a three-necked flask; phosgene gas was passed through the solution for 1 hour and the solution was then heated for 30 min on a steam bath. The solid which precipitated during the reaction was collected on a Buchner funnel and the mother liquor evaporated in vacuo to give additional product. The combined solids (containing Pd-C) were carefully dissolved in ethanol (25 ml) and water (10 ml) and stirred with Norit for about 1 hr. Filtration through Celite and concentration in vacuo yielded an almost colorless solid, (1.1 g). Recrystallization from ethanol:-water (5:1) yielded 0.85 g (32.3%) of the desired product G mp 288° (dec.).

B. D,L-3-(6-hydroxybenzimidazol-2-one-5-yl)alanine .HBr

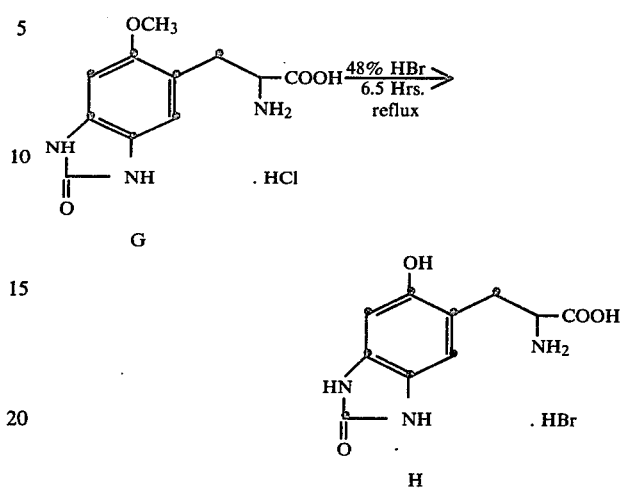

The amino acid G (0.600 g) was refluxed with 48% HBr (23 ml) for 6.5 hrs. using a Hg trap to exclude air. The solution was then evaporated in vacuo and the solid was dissolved in CH₃OH (40 ml) and treated with Norit for 1 hr. After filtering through Celite, the mother liquor was concentrated in vacuo to give a solid. The solid was recrystallized from CH₃OH:CH₃CN (1:2) to yield 432 mg (65%) of a colorless, solid compound H mp 268° (dec.).

The G and H compounds also include their tautomers.

HI can be used in place of HBr to effect the ether cleavage in Example 1, step F, or Example 2, step B and the resultant product will then be the HI salt.

The benzimidazole alanine product in Example 1, Step F or Example 2, step B is obtained as the HBr or HI salt. This salt may be conventionally neutralized to provide the free alanine base. The base can then be used as such as an antihypertensive agent or converted to any other suitable salt by treatment with appropriate acid or base.

Claims to the invention follow.
What is claimed is:
1. A compound having the formula

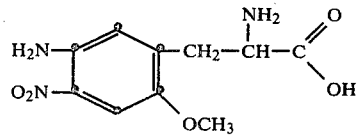

* * * * *